United States Patent

Moretti et al.

Patent Number: 5,968,252
Date of Patent: Oct. 19, 1999

[54] POLYCYCLIC COMPOUNDS

[75] Inventors: Robert Moretti, Vaulruz; Gary Wooden, Oberschrot, both of Switzerland

[73] Assignee: Ciba Specialty Chemicals Corporation, Tarrytown, N.Y.

[21] Appl. No.: 09/046,982

[22] Filed: Mar. 24, 1998

[30] Foreign Application Priority Data

Mar. 25, 1997 [CH] Switzerland ................ 715/97

[51] Int. Cl.$^6$ ................................. C08K 5/00

[52] U.S. Cl. ............... 106/498; 546/21; 546/23; 546/24; 546/79; 546/81; 546/155; 106/493

[58] Field of Search ................ 546/21, 23, 24, 546/79, 81, 155; 106/498, 493

[56] References Cited

U.S. PATENT DOCUMENTS

| | | | |
|---|---|---|---|
| 3,682,929 | 8/1972 | Siggel et al. | 546/155 |
| 4,782,153 | 11/1988 | Rochat et al. | 546/81 |
| 5,750,758 | 5/1998 | Zambounis et al. | 558/276 |
| 5,776,949 | 7/1998 | Cordi et al. | 514/312 |

OTHER PUBLICATIONS

G.P. Ellis, "Synthesis of Fused Heterocycles, Part 2", 1992, XP–002069951.

*Primary Examiner*—Mark L. Bell
*Assistant Examiner*—Scott L. Hertzog
*Attorney, Agent, or Firm*—David R. Crichton

[57] ABSTRACT

Compounds of formula

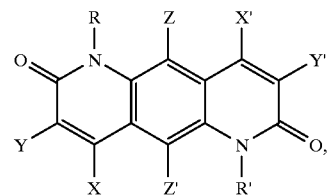

(I)

wherein R and R' are each independently of the other hydrogen, $C_1$–$C_{18}$alkyl, $COR_1$, $COR_2$ or $COOR_1$, X and X' are each independently of the other hydrogen, halogen, OH, $NH_2$, COOH, $C_1$–$C_{18}$-alkyl, isocyclic or heterocyclic aromatic radicals, $OR_3$, $OCOR_3$, $OCOR_4$, $OCOR_3$, $NHR_3$, $N(R_3)_2$, $NHCOR_3$, $NHCOR_4$ or $NHCOOR_3$, Y and Y' are each independently of the other hydrogen, halogen, OH, $NH_2$, nitro, cyano, $C_1$–$C_{18}$alkyl, isocyclic or heterocyclic aromatic radicals, $COR_5$, $COR_6$, $COOR_5$, $COOR_6$, $CONH_2$, $SO_2R_5$, $SO_2R_6$, $SO_2NH_2$, $SO_3H$, $PO(OR_5)_2$ or $PO(OH)_2$, and Z and Z' are each independently of the other hydrogen, halogen, OH, $NH_2$, COOH, cyano, $C_1$–$C_{18}$alkyl, isocyclic or heterocyclic aromatic radicals, $OR_7$, $OR_8$, $OCOR_7$, $OCOR_8$, $OCOOR_7$, $NHR_7$, $N(R_7)_2$, $NHR_8$, $CONH_2$, $NHCOR_7$, $NHCOR_8$ or $COOR_7$, $R_1$, $R_3$, $R_5$ and $R_7$ are each independently of one another $C_1$–$C_{18}$alkyl, and $R_2$, $R_4$, $R_6$ and $R_8$ are each independently of one another isocyclic or heterocyclic aromatic radicals, with the proviso that, if X and X' are OH, then Y and Y' cannot be hydrogen.

These compounds are excellently suitable as pigments for colouring high molecular weight organic material.

9 Claims, No Drawings

POLYCYCLIC COMPOUNDS

The present invention relates to novel polycyclic compounds of the pyrido-quinoline-dione-type (PCD) and to their use as pigments.

U.S. Pat. No. 3,682,929 describes the preparation of derivatives of aromatic bis(2,4-dihydroxy-pyridines) which are used as starting products for the preparation of colourants, including also 2,4,7,9-tetrahydropyrido-(2,3-g)-quinoline.

Surprisingly, it has now been found that certain compounds of the pyrido-quinoline-dione type have very good pigment properties and are therefore very suitable for colouring high molecular weight organic material.

Accordingly, this invention relates to compounds of formula

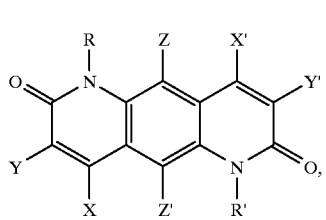

(I)

wherein R and R' are each independently of the other hydrogen, $C_1$–$C_{18}$alkyl, $COR_1$, $COR_2$ or $COOR_1$, X and X' are each independently of the other hydrogen, halogen, OH, $NH_2$, COOH, $C_1$–$C_{18}$-alkyl, isocyclic or heterocyclic aromatic radicals, $OR_3$, $OCOR_3$, $OCOR_4$, $OCOOR_3$, $NHR_3$, $N(R_3)_2$, $NHCOR_3$, $NHCOR_4$ or $NHCOOR_3$, Y and Y' are each independently of the other hydrogen, halogen, OH, $NH_2$, nitro, cyano, $C_1$–$C_{18}$alkyl, isocyclic or heterocyclic aromatic radicals, $COR_5$, $COR_6$, $COOR_5$, $COOR_6$, $CONH_2$, $SO_2R_5$, $SO_2R_6$, $SO_2NH_2$, $SO_3H$, $PO(OR_5)_2$ or $PO(OH)_2$, and Z and Z' are each independently of the other hydrogen, halogen, OH, $NH_2$, COOH, cyano, $C_1$–$C_{18}$alkyl, isocyclic or heterocyclic aromatic radicals, $OR_7$, $OR_8$, $OCOR_7$, $OCOR_8$, $OCOOR_7$, $NHR_7$, $N(R_7)_2$, $NHR_8$, $CONH_2$, $NHCOR_7$, $NHCOR_8$ or $COOR_7$, $R_1$, $R_3$, $R_5$ and $R_7$ are each independently of one another $C_1$–$C_{18}$alkyl, and $R_2$, $R_4$, $R_6$ and $R_8$ are each independently of one another isocyclic or heterocyclic aromatic radicals, with the proviso that, if X and X' are OH, then Y and Y' cannot be hydrogen.

Substituents defined as halogen are typically fluoro, iodo, in particular bromo and, preferably, chloro.

$C_1$–$C_{18}$Alkyl is typically methyl, ethyl, n-propyl, isopropyl, n-butyl, sec-butyl, tert-butyl, n-pentyl, tert-amyl, hexyl, heptyl, octyl, decyl, dodecyl, hexadecyl and octadecyl.

Isocyclic or heterocyclic aromatic radicals are understood as being preferably mono- to tetra-cyclic, in particular mono- or bicyclic radicals. Examples to be mentioned are:

Phenyl, diphenylyl, naphthyl and pyrenyl radicals. These radicals may contain conventional substituents which do not bring about water-solubility such as:

1) halogen atoms, typically chloro, bromo or fluoro
2) Alkyl groups, (preferably containing 1–6 carbon atoms). These may contain substituents which do not bring about water-solubility, for example fluoro atoms, hydroxyl or cyano groups or groups of formula —$OR_{10}$, —$OCOR_9$, —$COOR_9$, —$CONR_{10}R_{11}$ or —$R_9$—$OCONHR_9$, wherein $R_9$ is alkyl (preferably $C_1$–$C_6$alkyl), aryl, e.g. naphthyl, or phenyl, $C_5$–$C_6$cycloalkyl, aralkyl, in particular benzyl or a heterocyclic radical, each of which is unsubstituted or substituted by halogen, $C_1$–$C_6$alkyl or $C_1$–$C_6$alkoxy, $R_{10}$ and $R_{11}$ are H, alkyl, (in particular $C_1$–$C_6$alkyl), $C_2$–$C_6$cyanalkyl and hydroxyalkyl, $C_5$–$C_6$cycloalkyl, aryl or heteroaryl, in particular phenyl which is unsubstituted or substituted by halogen, $C_1$–$C_6$alkyl or $C_1$–$C_6$alkoxy, or wherein $R_{10}$ and $R_{11}$, together with the nitrogen atom are a 5–6-membered hetero ring, for example a morpholine or piperidine or phthalimide ring. Other substituents at the alkyl radicals to be mentioned are also mono- or dialkylated amino groups, preferably containing 2–6 carbon atoms, aryl radicals, e.g. naphthyl radicals or, in particular, phenyl radicals or heterocyclic aromatic radicals which are unsubstituted or substituted by halogen, $C_1$–$C_6$alkyl or $C_1$–$C_6$alkoxy, such as the 2-thienyl, 2-benzoxazolyl, 2-benzothiazolyl, 2-benzimidazolyl, 6-benzimidazolonyl, 2-, 3- or 4-pyridyl, 2-, 4- or 6-quinolyl radicals.

Examples to be mentioned of unsubstituted or substituted alkyl radicals are: methyl, ethyl, n-propyl, isopropyl, hexyl, propenyl, hydroxymethyl, trifluoromethyl, trifluoroethyl, cyanomethyl, methoxycarbonylmethyl, acetoxymethyl or benzyl.

3) The -$OR_{12}$ group, wherein $R_{12}$ is H, alkyl, preferably $C_1$–$C_6$alkyl, aryl, typically naphthyl or, in particular, phenyl, $C_5$–$C_6$cycloalkyl, aralkyl or a heterocyclic radical, each of which is unsubstituted or substituted by halogen, $C_1$–$C_6$alkyl or $C_1$–$C_6$alkoxy. Typical examples of $R_{12}$ to be mentioned are: hydrogen, methyl, ethyl, n-propyl, isopropyl, trifluoroethyl, phenyl, o-, m- or p-chlorophenyl, o-, m- or p-methylphenyl, α- or β-naphthyl, cyclohexyl, benzyl, thienylmethyl or pyranylmethyl.

4) The -$SR_{12}$ group, wherein $R_{12}$ has the meaning stated for 3). Typical examples of $R_{12}$ to be mentioned are: methyl, ethyl, n-propyl, isopropyl, phenyl, o-, m- or p-chlorophenyl, o-, m- or p-methylphenyl, 2- or β-naphthyl, cyclohexyl, benzyl, thienyl or pyranylmethyl.

5) The cyano group.

6) The group of formula —$NR_{10}R_{11}$ wherein $R_{10}$ and $R_{11}$ have the meaning stated for 2). Typical examples to be mentioned are: $NH_2$, methylamino, dimethylamino, ethylamino, diethylamino, isopropylamino, β-hydroyethylamino, β-hydroxypropylamino, N,N-bis(β-hydroxyethyl)amino, N,N-bis-β-cyanethyl)amino, cyclohexylamino, phenylamino, N-methylphenylamino, benzylamino, dibenzylamino, piperidyl or morpholyl.

7) The group of formula —$COOR_9$, wherein $R_9$ has the meaning stated for 2). Illustrative examples of $R_9$ to be mentioned are: methyl, ethyl, isopropyl, n-butyl, phenyl, benzyl or furfuryl.

8) The group of formula —$COR_{12}$ wherein $R_{12}$ has the meaning stated for 3). Typical examples of $R_{12}$ to be mentioned are: hydrogen, methyl, ethyl, phenyl, o-, m- or p-chlorophenyl, o-, m- or p-methylphenyl, or α- or β-naphthyl.

9) The group of formula —$NR_{13}$, $COR_9$ wherein $R_9$ has the meaning stated for 2), $R_{13}$ is hydrogen, alkyl, preferably $C_1$–$C_6$alkyl, aryl, typically naphthyl or, in particular, phenyl, $C_5$–$C_6$cyclo-alkyl, aralkyl, each of which is unsubstituted or substituted by halogen, $C_1$–$C_6$alkyl or $C_1$–$C_6$alkoxy, or the radical —$COR_9$, where two radicals —$COR_9$, together with the nitrogen atom, can form a heterocyclic ring. Illustrative examples to be mentioned are: acetylamino, propionylamino, butyrylamino, benzoylamino, p-chlorobenzoylamino, p-methylbenzoylamino, N-methylacetylamino, N-methylbenzoylamino, N-succinimido or N-phthalimido.

10) The group of formula —NR$_{12}$COOR$_9$, wherein R$_9$ and R$_{12}$ have the meaning stated for 2) and 3). The —NHCOOCH$_3$, NHCOOC$_2$H$_5$ or NHCOOC$_6$H$_5$ groups may be mentioned as examples.

11) The group of formula —NR$_{12}$CONR$_{10}$R$_{11}$, wherein R$_{12}$, R$_{10}$ and R$_{11}$ have the meaning stated for 3) and 2). Typical examples to be mentioned are: ureido, N$_2$methylureido, N$_2$-phenylureido or N$_2$-2', 4'-dimethylphenylureido.

12) The group of formula NHSO$_2$R$_9$, wherein R$_9$ has the meaning stated for 2). Illustrative examples to be mentioned are: methansulfonylamino, phenylsulfonylamino, p-toluylsulfonylamino or β-naphthylsulfonylamino.

13) The groups of formula —SO$_2$R$_9$ or SOR$_9$, wherein R$_9$ has the meaning stated for 2). Typical examples to be mentioned are: methylsulfonyl, ethylsulfonyl, phenylsulfonyl, 2-naphthylsulfonyl, phenylsulfoxidyl.

14) The group of formaul —SO$_2$OR$_{14}$, wherein R$_{14}$ is an aryl radical, in particular a phenyl radical which is unsubstituted or substituted by halogen, C$_1$–C$_6$alkyl or C$_1$–C$_6$alkoxy. Examples of R$_{14}$ to be mentioned are phenyl, o-, m- or p-chlorophenyl, o-, m- or p-methylphenyl, α- or β-naphthyl.

15) The group of formula —CONR$_{10}$R$_{11}$, wherein R$_{10}$ and R$_{11}$ have the meaning stated for 2). Illustrative examples to be mentioned are: carbamoyl, N-methylcarbamoyl, N-ethyl-carbamoyl, N-phenylcarbamoyl, N,N-dimethylcarbamoyl, N-methyl-N-phenylcarbamoyl, N-α-naphthylcarbamol or N-piperidylcarbamoyl.

16) The group of formula —SO$_2$NR$_{10}$R$_{11}$, wherein R$_{10}$ and R$_{11}$ have the meaning stated for 2). Typical examples to be mentioned are: sulfamoyl, N-methylsulfamoyl, N-ehtylsulfamoyl, N-phenylsulfamoyl, N-methyl-N-phenylsulfamoyi or N-morphoylsulfamoyl.

17) The group of formula —N=N—Q, wherein Q is the radical of a coupling component, or a phenyl radical which is unsubstituted OT substituted by halogen, C$_1$–C$_6$alkyl or C$_1$–C$_6$alkoxy. Examples of Q to be mentioned are the acetoacetarylide, pyrazolyl, pyridonyl, O- or p-hydroxyphenyl, o-hydroxynaphthyl, p-aminophenyl, or p-N,N-dimethylaminophenyl radicals.

18) The group of formula —OCOR$_9$ wherein R$_9$ has the meaning stated for 2). Examples of R$_9$ to be mentioned are methyl, ethyl, phenyl, o-, m- or p-chlorophenyl. 19) The group of formula —OCONHR$_9$ wherein R$_9$ has the meaning stated for 2). Examples of R$_9$ to be mentioned are methyl, ethyl, phenyl, o-, m or p-chrophenyl.

Particularly interesting compounds are those of formula I, wherein R and R' are each independently of the other hydrogen, C$_1$–C$_4$alkyl or COOR$_1$, X and X' are each independently of the other hydrogen, halogen, OH, NH$_2$, C$_1$–C$_4$alkyl, OR$_3$, OCOOR$_3$, NHCOOR$_3$ or a radical of formula

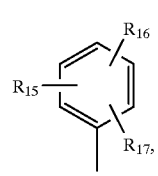

(II)

Y and Y' are each independently of the other hydrogen, halogen, NH$_2$, nitro, cyano, C$_1$–C$_4$-alkyl, COR$_5$, COR$_6$, COOR$_5$, CONH$_2$, unsubstituted or C$_1$–C$_4$alkyl-substituted diphenylyl, naphthyl, phenanthrenyl, anthracenyl, pyrenyl or pyridinyl, or a radical of formula

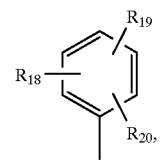

(III)

Z and Z' are each independently of the other hydrogen, halogen, COOH, cyano, C$_1$–C$_4$alkyl, OR$_7$, COOR$_7$, CONH or a radical of formula

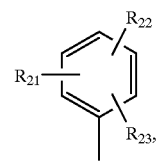

(IV)

R$_1$, R$_3$, R$_5$ and R$_7$ are each independently of one another C$_1$–C$_4$alkyl, and R$_6$ is a radical of formula

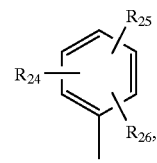

(V)

and

R$_{15}$, R$_{16}$, R$_{17}$, R$_{18}$, R$_{19}$, R$_{20}$, R$_{21}$, R$_{22}$, R$_{23}$, R$_{24}$, R$_{25}$ and R$_{26}$ are each independently of one another hydrogen or halogen atoms, carbamoyl, cyano, nitro, trifluoromethyl or C$_2$–C$_6$alkylcarba-moyl groups, alkyl, alkoxy, alkylamino or alkylmercapto groups containing 1–6 carbon atoms, hydroxycarbonyl groups, alkoxycarbonyl or alkanoylamino groups containing 2–6 carbon atoms, phenoxy, phenylmercapto, phenoxycarbonyl, phenylcarbamoyl or benzoylamino groups which are unsubstituted or substituted by halogen, alkyl or alkoxy containing 1–6 carbon atoms, at least one of the substituents R$_{15}$, R$_{16}$ and R$_{17}$ in formula II, at least one of the substituents R$_{18}$, R$_{19}$ and R$_{20}$ in formula III, at least one of the substituents R$_{21}$, R$_{22}$ and R$_{23}$ in formula IV and at least one of the substituents R$_{24}$, R$_{25}$ and R$_{26}$ in formula V being hydrogen.

Preferred compounds are those of formula I, wherein

R and R' are each independently of the other hydrogen, C$_1$–C$_4$alkyl or COOR$_1$, X and X' are each independently of the other hydrogen, halogen, OH, NH$_2$, C$_1$–C$_4$alkyl or a radical of formula

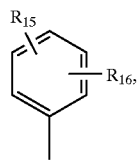
(VI)

Y and Y' are each independently of the other hydrogen, cyano, $C_1$–$C_4$alkyl, $COR_5$ $COR_6$, $COOR_5$, $CONH_2$, unsubstituted or $C_1$–$C_4$alkyl-substituted diphenylyl, naphthyl, phenanthenyl or pyridinyl, or a radical of formula

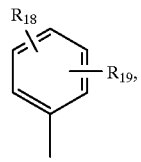
(VII)

Z and Z' are each independently of the other hydrogen halogen, $C_1$–$C_3$alkyl or $OR_7$, $R_1$, $R_5$ and $R_7$ are each independently of one another $C_1$–$C_4$alkyl, and $R_6$ is a radical of formula

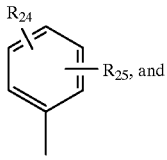
(VIII)

$R_{15}$, $R_{16}$, $R_{18}$, $R_{19}$, $R_{24}$ and $R_{25}$ are each independently of one another a hydrogen, chloro or bromo atom, a methyl, cyano, nitro, alkylamino or alkoxy group containing 1–4 carbon atoms, a phenoxy group which is unsubstituted or substituted by chloro or methyl, a hydroxycarbonyl group, an alkoxycarbonyl or alkyl-carbamoyl group containing 2–5 carbon atoms, or a phenylcarbamoyl group which is unsubstituted or substituted by chloro, methyl or methoxy.

$R_{15}$, $R_{18}$ and $R_{24}$ are preferably in p-position and are preferably methyl, chloro, cyano or methoxy, and $R_{16}$, $R_{19}$ and $R_{25}$ are preferably hydrogen.

Particularly preferred compounds of formula I are those, wherein R=R',X=X',Y=Y,' and Z=Z'.

Very particularly preferred compounds are those of formula

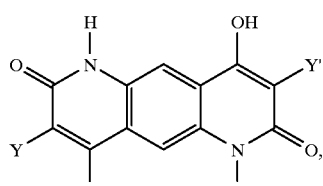
(IX)

wherein Y and Y' are equal and are diphenylyl, naphthyl, phenantrenyl, pyridinyl or, preferably, a radical of formula

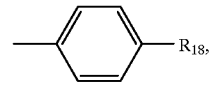

wherein $R_{18}$ is hydrogen, methoxy, chloro, bromo, cyano, nitro, dimethylamino, hydroxycarbonyl or methoxycarbonyl.

The preparation of the novel compounds of formula I is carried out in general analogy to commonly known methods, e.g.

by reacting a compound of formula (X)

RHN / COOA
AOOC / NHR'
Z, Z' with 1 equivalent each of a compound of formula

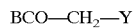 (XIa) and

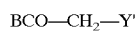 (XIb)

to a compound of formula (XII)

with subsequent ring closure, e.g. by treatment with NaH, to the compound of formula

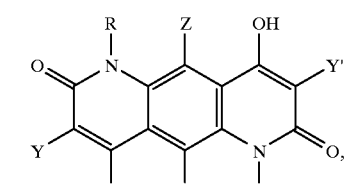
(XIII)

by reacting a compound of formula

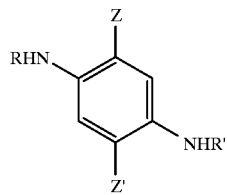
(XIV)

with 1 equivalent each of a compound of formula

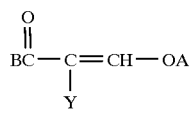
(XVa)

and

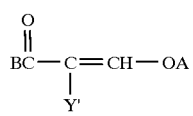
(XVb)

to a compound of formula

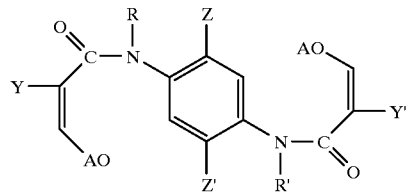
(XVI)

with subsequent ring closure to the compound of formula

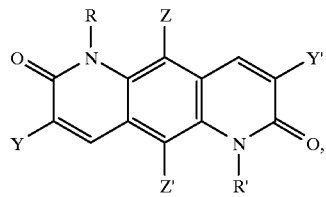
(XVII)

compound of formula XIV with 1 equivalent each of a compound of formula

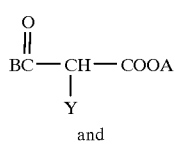
(XVIIIa)

and

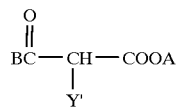
(XVIIIb)

to a compound of formula

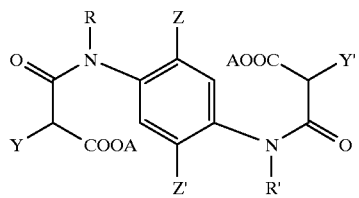
(XIX)

with subsequent ring closure to a compound of formula XIII, or by reacting a compound of formula XIV with 1 equivalent each of a compound of formula

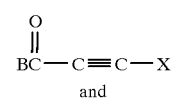
(XXa)

and

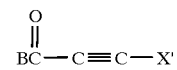
(XXb)

to a compound of formula

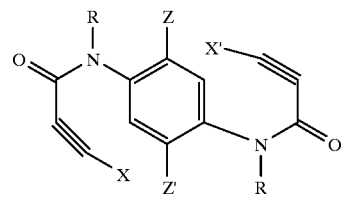
(XXI)

with subsquent ring closure to a compound of formula

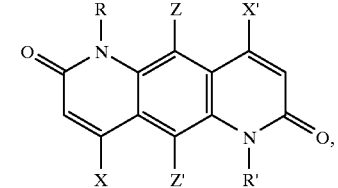
(XXII)

R, R', X, X', Y, Y' and Z, Z' each having the meaning cited above, and A being $C_1$–$C_3$alkyl and B being OH or chloro.

The starting compounds of formulae X, XIa and b, XIV, XVa and b, XVIIIa and b and XX a and b are known. Should any of them still be novel, they can be prepared by methods known per se.

Depending on the type of their substituents and on the polymer to be coloured, the compounds of formula I can be used as polymer-soluble colourants or, preferably, as pigments for colouring high molecular weight organic material. In the latter case it is advantageous to convert the products obtained from synthesis to a finely dispersed form. This may be achieved in different manner, for example:

a) by grinding or kneading, conveniently in the presence of grinding assistants, such as inorganic or organic salts, with or without the addition of organic solvents. After grinding, the assistants are removed in conventional manner, soluble inorganic salts e.g. with water, and water-insoluble organic solvents e.g. by steam distillation, b) by precipitation from sulfuric acid, methanesulfonic acid, trichloroacetic acid or polyphosphoric acid.

c) by converting the crude pigment into an alkali metal salt or amine salt and hydrolysing the latter. This is effected, for example, by mixing the crude pigment with a base, for example with alkali hydroxide or alkali alcoholate, ammonia or with amine in a polar organic solvent such as dimethylformamide, the pigment dissolving partially or completely. The pigment is precipitated by hydrolysis, preferably by acidifying the solution which is filtered, where appropriate.

It may be found to be convenient to aftertreat the crude pigments or the pigments treated according to a), b) or c) with organic solvents, preferably with solvents boiling above 100° C.

Particularly suitable compounds have been found to be benzenes which are substituted by halogen atoms, alkyl groups or nitro groups, such as xylenes, chlorobenzene, o-dichlorobenzene or nitrobenzene as well as pyridine bases, such as pyridine, picoline or quinoline, and also ketones, such as cyclohexanone, ethers such as 2-methoxyethanol or 2-ethoxyethanol, amides, such as dimethylformamide or N-methylpyrrolidone, and also dimethylsulfoxide, sulfolane or water by itself, if required under pressure. The aftertreatment can also be carried out in water in the presence of organic solvents and/or with addition of surfactants or liquid ammonia or aliphatic amines.

Illustrative examples of high molecular weight organic materials which can be coloured or pigmented with the novel pigments are cellulose ethers and esters, typically ethyl cellulose, nitro cellulose, cellulose acetate, cellulose butyrate, natural resins or synthetic resins, typically polymerisation resins or condensation resins, such as aminoplasts, preferably urea/formaldehyde resins and melamine/formaldehyde resins, alkyd resins, phenolic plastics, polycarbonates, polyolefins, polystyrene, polyvinyl chloride, polyamides, polyurethanes, polyester, ABS, polyphenylene oxides, rubber, casein, silicone and silicone resins, singly or in mixtures.

The above high molecular weight organic compounds may be obtained singly or as mixtures as plastics, melts or in the form of spinning solutions, paints, coating materials or printing inks. Depending on the end use requirement, it is expedient to use the pigments of this invention as toners or in the form of preparations.

The pigments of this invention can be used in an amount of 0.01 to 30% by weight, preferably of 0.1 to 10% by weight, based on the high molecular weight organic material to be pigmented.

The pigmenting of the high molecular weight organic substances with the pigments of this invention is conveniently effected by incorporating them by themselves or in the form of masterbatches in the substrates using roll mills, mixing or milling apparatus. The pigmented material is then brought into the desired final form by methods which are known per se, conveniently by calendering, moulding, extruding, coating, casting or by injection moulding. It is often desirable to incorporate plasticisers into the high molecular weight compounds before processing in order to produce non-brittle mouldings or to diminish their brittleness. Suitable plasticisers are typically esters of phosphoric acid, phthalic acid or sebacic acid. The plasticisers may be incorporated into the novel pigment compositions before or after working the pigments into the polymers. To obtain different shades, it is also possible to add to the high molecular weight organic materials fillers or other chromophoric components such as white, coloured or black pigments in any amount, in addition to the novel pigments compositions.

For pigmenting paints, coating materials and printing inks, the high molecular weight organic materials and the pigments of this invention, together with optional additives such as fillers, other pigments, siccatives or plasticisers, are finely dispersed or dissolved in a common organic solvent or solvent mixture. The procedure may be such that the individual components by themselves, or also several jointly, are dispersed or dissolved in the solvent and thereafter all the components are mixed.

The novel pigments are particularly suitable for colouring plastics, more particularly polyvinyl chloride and polyolefins, and paints, preferably automotive and paints.

When used for colouring e.g. polyvinyl chloride or polyolefins, the novel pigments are distinguished by a yellow to brown shade, good allround pigment properties, such as good dispersibility, superior colour strength and purity, good fastness to migration, heat, light and weathering as well as good opacity.

The invention is illustrated by the following Examples. Preparation of Intermediates of the General Formula

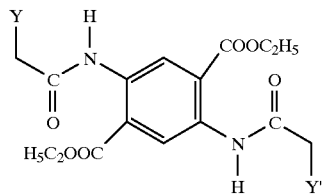

(XXIII)

EXAMPLE 1

1:14.8 g (187.5 mmol) of pyridine and 100 mg of 4-dimethylaminopyridine are added to a slurry consisting of 18.9 g (75 mmol) of diethyl 2,5-diaminoterephthalate in 300 ml of dichloromethane. After cooling the reaction mixture in an ice bath and adding 27.8 g (180 mmol) of phenacetyl chloride over 45 minutes, it is then heated to room temperature and stirred for another 16 hours before being poured into 10% aqueous $Na_2CO_3$. The organic phase is washed with 1N aqueous hydrochloric acid and dried over $MgSO_4$. The crude product is recrystallised from ethyl acetate/hexane, affording 31 g (85% of theory) of a pale yellow solid substance of formula XXIII, wherein Y and Y' are phenyl. Analysis: $^1$H-NMR (DMSO-$d_6$): 1.25 (t, 6H, J=7 Hz); 3.72 (s, 4H); 4.24 (q, 4H, J=7 Hz); 7.25–7.40 (m, 10H); 8.57 (s, 2H); 10.47 (s, 2H).

EXAMPLE 2

The procedure of Example 1 is repeated, with the sole exception of replacing phenacetyl chloride with the equivalent amount of 4-methoxyphenylacetyl chloride. A 81% yield of the compound of formula XXIII is obtained, wherein Y and Y' are 4-methoxyphenyl.
Analysis:
$^1$H-NMR (CDCl$_3$): 1.38 (t, 6H, J=7Hz); 3.69 (s, 4H); 3.80 (s, 6H); 4.33 (q, 4H, J=7); 6.90 (d, 4H, J=8.6 Hz); 7.26 (s, 2H); 7.28 (d, 4H, J=8.6 Hz); 10.88 (s, 2H).

EXAMPLE 3

The procedure of Example 1 is repeated, with the sole exception of replacing phenacetyl chloride with the equivalent amount of 4-nitrophenylacetyl chloride. An 88% yield of the compound of formula XXIII is obtained, wherein Y and Y' are 4-nitrophenyl.
Analysis:
$^1$H-NMR (DMSO-d$_6$): 1.27 (t, 6H, J=7 Hz); 3.93 (s, 4H); 4.25 (q, 4H, J=7 Hz); 7.62 (d, 4H, J=8.6 Hz); 8.22 (d, 4H, J=8.6 Hz); 8.46 (s, 2H); 10.54 (s, 2H).

EXAMPLE 4

7.83 g (43.7 mmol) of 4-dimethylaminophenylacetic acid, 4.59 g (18.2 mmol) of diethyl 2,5-diaminoterephthalate and 1.11 g (9.1 mmol) of 4-dimethylaminopyridine are dissolved under nitrogen in 200 ml of anhydrous dichloromethane. The solution is cooled in an ice bath and then 9.02 g (43.7 mmol) of dicyclohexylcarbodiimide are added in increments. The ice bath is then removed and the reaction mixture is stirred for 16 hours at room temperature. The resulting precipitate is isolated by filtration and washed with dichloromethane, and the solvent is then separated from the filtrate by distillation. The residue is made into a slurry in 300 ml of ethanol and refluxed for 2 hours. After cooling to room temperature, the precipitated solid substance is isolated by filtration, washed with ethanol and dried, giving 9.23 g (88% of theory) of a white product of formula XXIII, wherein Y and Y' are 4-(N,N-dimethylamino)phenyl.
Analysis:
$^1$H-NMR (DMSO-d$_6$): 100° C.): 1.28 (t, 6H, J=7 Hz); 2.86 (s, 12H); 3.56 (s, 4H); 4, 28 (q, 4H, J=7 Hz); 6.69 (m, 4H); 7.13 (m, 4H); 8.72 (s, 2H); 10.13 (wide s, 2H).

EXAMPLE 5

The procedure of Example 4 is repeated, with the sole exception of replacing 4-dimethylaminophenylacetic acid with the equivalent amount of 4-diphenylacetic acid. A 99% yield of the compound of formula XXIII is obtained, wherein Y and Y' are 4-diphenyl.
Analysis:
$^1$H-NMR (DMSO-d$_6$):1.24 (t, 6H, J=7 Hz); 3.77 (s, 4H); 4.25 (q, 4H, J=7 Hz); 7.33–7.49 (m, 10H); 7.63–7.68 (m, 8H); 8.57 (s, 2H); 10.52 (s, 2H).

EXAMPLE 6

The procedure of Example 4 is repeated, with the sole exception of replacing 4-dimethylaminophenylacetic acid with the equivalent amount of 4-bromophenylacetic acid. A 95% yield of the compound of formula XXIII is obtained, wherein Y and Y' are 4-bromophenyl.
Analysis:
$^1$H-NMR (DMSO-d$_6$): 1.25 (t, 6H, J=7 Hz); 3.72 (s, 4H); 4.25 (q, 4H, J=7 Hz); 7.30 (d, 4H, J=8.6 Hz); 7.54 (d, 4H, J=8.6 Hz); 8.50 (s, 2H); 10.47 (s, 2H).

EXAMPLE 7

The procedure of Example 4 is repeated, with the sole exception of replacing 4-dimethylaminophenylacetic acid with the equivalent amount of 1-naphthylacetic acid. A 95% yield of the compound of formula XXIII is obtained, wherein Y and Y' are 1-naphthyl.
Analysis:
$^1$H-NMR (DMSO-d$_6$): 1.19 (t, 6H, J=7 Hz); 4.17 (q, 4H, J=7 Hz); 4.21 (s, 4H); 7.47–7.57 (m, 8H); 7.87–8.07 (m, 6H); 8.61 (s, 2H); 10.53 (s, 2H).

EXAMPLE 8

The procedure of Example 4 is repeated, with the sole exception of replacing 4-dimethylaminophenylacetic acid with the equivalent amount of 2-naphthylacetic acid. A 85% yield of the compound of formula XXIII is obtained, wherein Y and Y' are 2-naphthyl.
Analysis:
$^1$H-NMR (DMSO-d$_6$): 1.19 (t, 6H, J=7 Hz); 3.90 (s, 4H); 4.20 (q, 4H, J=7 Hz); 746–7.54 (m, 6H); 7.86–7.91 (m, 8H); 8.57 (s, 2H); 10.54 (s, 2H).

EXAMPLE 9

The procedure of Example 4 is repeated, with the sole exception of replacing 4-dimethylaminophenylacetic acid with the equivalent amount of 1-pyrenylacetic acid. A 89% yield of the compound of formula XXIII is obtained, wherein Y and Y' are 1-pyrenyl.
Analysis:
$^1$H-NMR (DMSO-d$_6$): 1.05 (t, 6H, J=7 Hz); 4.05 (q, 4H, J=7 Hz); 4.51 (s, 4H); 8.07–8.34 (m, 18H); 8.59 (s, 2H); 10.56 (s, 2H).

EXAMPLE 10

The procedure of Example 4 is repeated, with the sole exception of replacing 4-dimethylaminophenylacetic acid with the equivalent amount of 4-nitro-1-naphthylacetic acid. A 27% yield of the compound of formula XXIII is obtained, wherein Y and Y' are 4-nitro-1-naphthyl.
Analysis:
$^1$H-NMR (DMSO-d$_6$): 1.20 (t, 6H, J=Hz); 4.19 (q, 4H, J=7 Hz); 4.40 (s, 4H); 7.70–7.80 (m, 6H); 8.27–8.37 (m, 6H); 8.51 (s, 2H); 10.61 (s, 2H).

EXAMPLE 11

The procedure of Example 4 is repeated, with the sole exception of replacing 4-dimethylaminophenylacetic acid with the equivalent amount of 2-pyridylacetic acid hydrochloride and triethylamine. A 68% yield of the compound of formula XXIII is obtained, wherein Y and Y' are 2-pyridyl.
Analysis:
$^1$H-NMR (CDCl$_3$): 1.39 (t, 6H, J=7 Hz); 3.96 (s, 4H); 4.37 (q, 4H, J=7 Hz); 7.20–7.25 (m, 2H); 7.36 (d, 2H, J=7.8 Hz); 7.69 (m, 2H); 8.63 (m, 2H); 9.34 (s, 2H); 11, 21 (s, 2H).
Preparation of the end products of the general formula

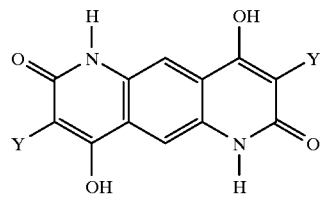

(XXIV)

EXAMPLE 12

11.39 g (17.78 mmol) of the product of Example 5 are made into a slurry in 160 ml of anhydrous dimethylformamide under nitrogen. At the same time, 3.49 g (~80 mmol) of NaH (55–65% in mineral oil) are added to the slurry and the reaction mixture is then stirred for 20 minutes in an ultrasonic bath and is then heated for 3 hours to 100° C. in an oil bath. The mixture is cooled to 0° C. and is then poured into ice-cold aqueous hydrochloric acid (160 mmol in 2 l of water). The solid yellow product is isolated by filtration, washed with water, dried and is then made into a slurry in 300 ml of dimethylformamide. This slurry is heated for 1 hour to 110° C. and is then cooled to room temperature and filtered. The residue is washed with dimethylformamide and dried. After suspending the residue in 400 ml of ethanol/dichloromethane 1:1 and refluxing it overnight, it is isolated again by filtration, washed with ethanol and dried. 8.34 g (86% of theory) of a yellow solid substance of formula XXIV are obtained, wherein Y and Y' are 4-diphenyl.
Analysis:
$^1$H-NMR (DMSO-d$_6$): 7.37–7.54 (m, IOH); 7.74 (m, 8H); 7.83 (s, 2H); 10.28 (s, 2H); 11.55 (s, 2H).

EXAMPLE 13

The procedure of Example 12 is repeated, with the sole exception of replacing the product of Example 5 with the equivalent amount of the product of Example 1 as starting product. A 84% yield of a yellow solid substance of formula XXIV is obtained, wherein Y and Y' are phenyl.
Analysis:
mass spectroscopy: 396 (m$^+$, 100%)

EXAMPLE 14

The procedure of Example 12 is repeated, with the sole exception of replacing the product of Example 5 with the equivalent amount of the product of Example 2 as starting product. A 59% yield of a yellow solid substance of formula XXIV is obtained, wherein Y and Y' are 4-methoxyphenyl.
Analysis:
mass spectroscopy: 456 (m$^+$, 100%)

EXAMPLE 15

The procedure of Example 12 is repeated, with the sole exception of replacing the product of Example 5 with the equivalent amount of the product of Example 4 as starting product. A 55% yield of a yellow solid substance of formula XXIV is obtained, wherein Y and Y' are 4-dimethylamino.
Analysis:
$^1$H-NMR (DMSO-d$_6$): 2.95 (s, 12H); 6.80 (d, 4H, J=8.6 Hz); 7.23 (d, 4H, J=8.6 Hz); 7.73 (s, 2H); 9.78 (s, 2H); 11.37 (s, 2H).

EXAMPLE 16

The procedure of Example 12 is repeated, with the sole exception of replacing the product of Example 5 with the equivalent amount of the product of Example 3 as starting product. A 91% yield of a yellow solid substance of formula XXIV is obtained, wherein Y and Y' are 4-nitrophenyl.
Analysis:
$^1$H-NMR (DMSO-d$_6$, 100° C.): 7.72 (m, 4H); 7.91 (s, 2H); 8.23 (m, 4H); 11.22 (wide s, 2H).

EXAMPLE 17

The procedure of Example 12 is repeated, with the sole exception of replacing the product of Example 5 with the equivalent amount of the product of Example 7 as starting product. An 87% yield of a yellow solid substance of formula XXIV is obtained, wherein Y and Y' are 1-naphthyl.

Analysis:
$^1$H-NMR (DMSO-d$_6$): 7.43–7.63 (m, 8H); 7.97 (s, 2H); 7.98–8.02 (m, 6H); 10.09 (s, 2H); 11.55 (s, 2H).

EXAMPLE 18

The procedure of Example 12 is repeated, with the sole exception of replacing the product of Example 5 with the equivalent amount of the product of Example 8 as starting product. A 73% yield of a yellow solid substance of formula XXIV is obtained, wherein Y and Y' are 2-naphthyl.
Analysis:
$^1$H-NMR (DMSO-d$_6$): 7.54 (m, 6H); 7.87 (s, 2H); 7.95 (m, 8H); 10.27 (s, 2H); 11.56 (s, 2H).

EXAMPLE 19

The procedure of Example 12 is repeated, with the sole exception of replacing the product of Example 5 with the equivalent amount of the product of Example 6 as starting product. An 85% yield of a yellow solid substance of formula XXIV is obtained, wherein Y and Y' are 4-bromophenyl.
Analysis:
$^1$H-NMR (DMSO-d$_6$): 7.35 (d, 4H, J=8.4 Hz); 7.62 (d, 4H, J=8.4 Hz); 7.81 (s, 2H); 10.33 (s, 2H); 11.52 (s, 2H).

EXAMPLE 20

The procedure of Example 12 is repeated, with the sole exception of replacing the product of Example 5 with the equivalent amount of the product of Example 9 as starting product. A 91% yield of a yellow solid substance of formula XXIV is obtained, wherein Y and Y' are 1-pyrenyl.
Analysis:
$^1$H-NMR (DMSO-d$_6$): 7.89–8.38 (m, 18H); 8.27 (s, 2H); 10.17 (s, 2H); 11.66 (s, 2H).

EXAMPLE 21

The procedure of example 12 is repeated, with the sole exception of replacing the product of Example 5 with the equivalent amount of the product of Example 10 as starting product. An 87% yield of a yellow solid substance of formula XXIV is obtained, wherein Y and Y' are 4-nitro-1-naphthyl.
Analysis:
$^1$H-NMR (DMSO-d$_6$): 7.65 (m, 4H); 7.82 (m, 4H); 7.92 (s, 2H); 8.35–8.42 (m, 4H); 10.54 (wide s, 2H); 11.65 (s, 2H).

EXAMPLE 22

The procedure of Example 12 is repeated, with the sole exception of replacing the product of Example 5 with the equivalent amount of the product of Example 11 as starting product. A 58% yield of a yellow solid substance of formula XXIV is obtained, wherein Y and Y' are 2-pyridyl.
Analysis:
$^1$H-NMR (DMSO-d$_6$): 7.38 (m, 2H); 7.97 (s, 2H); 8.09 (m, 2H); 8.53 (m, 2H); 9.38 (m, 2H).

EXAMPLE 23

A mixture consisting of 8.31 g (15 mmol) of the product of Example 19, 2.36 g (9 mmol) of triphenylphosphine, 6.07 g (60 mmol) of triethylamine and 0.266 g (1.5 mmol) of PdCl$_2$ in 200 ml of N-methylpyrrolidone and 15 ml of methanol is stirred for 24 hours under CO pressure (15 bar) at 120° C. in autoclave. After cooling to room temperature, the reaction mixture is poured into aqueous hydrochloric acid (120 mmol HCl in 2 l of water). After filtration, the residue is washed first with water and dried and is then suspended in 300 ml of methanol and refluxed for 2 hours. After another filtration, the residue is washed with ether and dried and is then made into a slurry in 100 ml of dimethylformamide which is then heated for 2 hours to 100° C. After cooling to room temperature and subsequent filtration, the residue obtained is washed with dimethylformamide and dichloromethane and dried, giving 3.74 g (49% of theory) of a yellow solid substance of formula XXIV, wherein Y and Y' are a

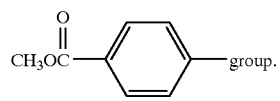group.

Analysis:
$^1$H-NMR (DMSO-$d_6$): 3.90 (s, 6H); 7.57 (d, 4H, J=8.2 Hz); 7.84 (s, 2H); 8.01 (d, 4H, J=8.2 Hz).

EXAMPLE 24

2.74 g (5.35 mmol) of the product of Example 23 are made into a slurry in 100 ml of ethanol and are charged with 100 ml of a 2N aqueous sodium hydroxide solution. This mixture is then refluxed for 2 hours under nitrogen. After cooling to room temperature, the reaction mixture is washed in a separating funnel with 100 ml of ethyl acetate and 100 ml of ether and is then filtered through Whatmann paper. The clear filtrate is acidified with 2N aqueous hydrochloric acid to pH 1. The precipitated product is isolated by filtration, washed with water and dried, affording 2.5 g (100% of theory) of a yellow solid substance of formula XXIV, wherein Y and Y' are a

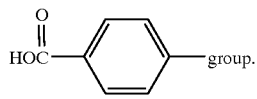group.

Analysis:
$^1$H-NMR (DMSO-$d_6$): 7.53 (d, 4H, J=8.4 Hz); 7.84 (s, 2H); 8.1 (d, 4H, J=8.4 Hz); 10.43 (wide s, 2H), 11.57 (s, 2H).

EXAMPLE 25

8.31 g (15 mmol) of the product of Example 19 and 4.03 g (45 mmol) of CuCN are heated for 20 hours in anhydrous N-methylpyrrolidone to 200° C. After cooling to 100° C., the reaction mixture is poured in 200 ml of 10% warm aqueous NaCN. After cooling further to room temperature, 5 ml of acetic acid are carefully added to the dark solution upon which a solid substance precipitates. The solid product is isolated by filtration, washed with warm water and dried in the air. Subsequently, it is made into a slurry in 250 ml of dimethylformamide and heated for 2 hours to 100° C. It is then cooled again to room temperature, isolated by filtration, washed with dimethylformamide and ethanol and dried. The dry product is suspended in 500 ml of chloroform, refluxed for 3 hours and is then isolated warm by filtration, washed with chloroform and dried, giving 6.05 g (90% of theory) of a solid yellow substance of formula XXIV, wherein Y and Y' are 4-cyanophenyl.
Analysis:
$^1$H-NMR (DMSO-$d_6$): 7.62 (d, 4H, J=8.3 Hz); 7.85 (s, 2H); 7.89 (d, 4H, J=8.3 Hz); 10.63 (wide s, 2H), 11.61 (s, 2H).

EXAMPLE 26a)

5.04 g of β-ethoxyacryloyl chloride are added to a solution consisting of 1.63 g of 1,4-phenylenediamine in 40 ml of N-methylpyrrolidone over 40 minutes at 25–30° C. 3.66 g of pyridine are then added dropwise over 20 minutes, the temperature being kept at 25–300° C. by external cooling. The suspension is then stirred for 24 hours at room-temperature and is then filtered. The filter cake is washed in succession with 50 ml of ethyl acetate, 50 ml of methanol and 50 ml of water and is dried at 80° C. in a vacuum drying oven, affording 2.5 g of the product of formula

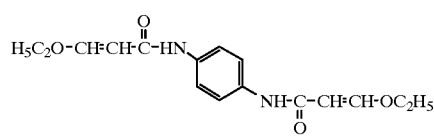

| | (m.p. >300° C.) | | |
|---|---|---|---|
| Analysis: | C | H | N |
| calculated: | 63.14% | 6.62% | 9.20% |
| found: | 62.32% | 6.80% | 9.01% | b) 0.7 g of the product of a) is heated for 6 hours at 120° C. in 20 g of polyphosphoric acid. The reaction mixture is then cooled, poured into ice water and filtered. The residue is suspended in 70 ml of ethanol and heated for 1 hour at 70° C. The resulting product is isolated by filtration and dried at 45° C. in a vacuum drying oven, affording 0.12 g of a brown solid substance of formula

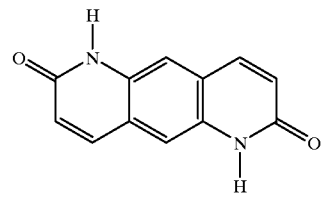

| Analysis: | C | H | N |
|---|---|---|---|
| calculated: | 67.92% | 3.80% | 13.20% |
| found: | 65.32% | 4.00% | 11.97% |

What is claimed is:
1. A compound of formula

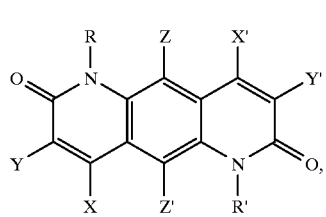

(I)

wherein R and R' are each independently of the other hydrogen, $C_1$–$C_{18}$alkyl, $COR_1$, $COR_2$ or $COOR_1$, X and X' are each independently of the other hydrogen, halogen, OH, $NH_2$, COOH, $C_1$–$C_{18}$-alkyl, isocyclic or heterocyclic aromatic radicals, $OR_3$, $OCOR_3$, $OCOR_4$, $OCOOR_3$, $NHR_3$, $N(R_3)_2$, $NHCOR_3$, $NHCOR_4$ or $NHCOOR_3$, Y and Y' are each independently of the other hydrogen, halogen, OH, $NH_2$, nitro, cyano, $C_1$–$C_{18}$alkyl, isocyclic or heterocyclic aromatic radicals, $COR_5$, $COR_6$, $COOR_5$, $COOR_6$, $CONH_2$, $SO_2R_5$, $SO_2R_6$, $SO_2NH_2$, $SO_3H$, $PO(OR_5)_2$ or $PO(OH)_2$, and Z and Z' are each independently of the other hydrogen, halogen, OH, $NH_2$, COOH, cyano, $C_1$–$C_{18}$alkyl, isocyclic or heterocyclic aromatic radicals, $OR_7$, $OR_8$, $OCOR_7$, $OCOR_8$, $OCOOR_7$, $NHR_7$, $N(R_7)_2$, $NHR_8$, $CONH_2$, $NHCOR_7$, $NHCOR_8$ or $COOR_7$, $R_1$, $R_3$, $R_5$ and $R_7$ are each independently of one another $C_1$–$C_{18}$alkyl, and $R_2$, $R_4$, $R_6$ and $R_8$ are each independently of one another isocyclic or heterocyclic aromatic radicals, with the proviso that, if X and X' are OH, then Y and Y' cannot be hydrogen.

2. A compound according to claim 1 of formula I, wherein R and R' are each independently of the other hydrogen, $C_1$–$C_4$alkyl or $COOR_1$, X and X' are each independently of the other hydrogen, halogen, OH, $NH_2$, $C_1$–$C_4$alkyl, $OR_3$, $OCOOR_3$, $NHCOOR_3$ or a radical of formula

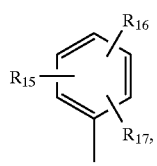

(II)

Y and Y' are each independently of the other hydrogen, halogen, $NH_2$, nitro, cyano, $C_1$–$C_4$-alkyl, $COR_5$, $COR_6$, $COOR_5$, $CONH_2$, unsubstituted or $C_1$–$C_4$alkyl-substituted diphenylyl, naphthyl, phenanthrenyl, anthracenyl, pyrenyl or pyridinyl, or a radical of formula

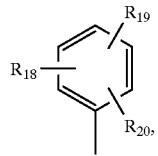

(III)

Z and Z' are each independently of the other hydrogen, halogen, COOH, cyano, $C_1$–$C_4$alkyl, $OR_7$, $COOR_7$, CONH or a radical of formula

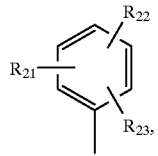

(IV)

$R_1$, $R_3$, $R_5$ and $R_7$ are each independently of one another $C_1$–$C_4$alkyl, and $R_6$ is a radical of formula

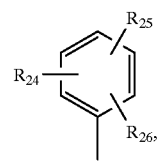

(V)

and $R_{15}$, $R_{16}$, $R_{17}$, $R_{18}$, $R_{19}$, $R_{20}$, $R_{21}$, $R_{22}$, $R_{23}$, $R_{24}$, $R_{25}$ and $R_{26}$ are each independently of one another hydrogen or halogen atoms, carbamoyl, cyano, nitro, trifluoromethyl or $C_2$–$C_6$alkylcar-bamoyl groups, alkyl, alkoxy, alkylamino or alkylmercapto groups containing 1–6 carbon atoms, hydroxycarbonyl groups, alkoxycarbonyl or alkanoylamino groups containing 2–6 carbon atoms, phenoxy, phenylmercapto, phenoxycarbonyl, phenylcarbamoyl or benzoylamino groups which are unsubstituted or substituted by halogen, alkyl or alkoxy containing 1–6 carbon atoms, at least one of the substituents $R_{15}$, $R_{16}$ and $R_{17}$ in formula II, at least one of the substituents $R_{18}$, $R_{19}$ and $R_{20}$ in formula III, at least one of the substituents $R_{21}$, $R_{22}$ and $R_{23}$ in formula IV and at least one of the substituents $R_{24}$, $R_{25}$ and $R_{26}$ in formula V being hydrogen.

3. A compound according to claim 2 of formula I, wherein R and R' are each independently of the other hydrogen, $C_1$–$C_4$alkyl or $COOR_1$, X and X' are each independently of the other hydrogen, halogen, OH, $NH_2$, $C_1$–$C_4$alkyl or a radical of formula

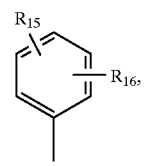

(VI)

Y and Y' are each independently of the other hydrogen, cyano, $C_1$–$C_4$alkyl, $COR_5$ $COR_6$, $COOR_5$, $CONH_2$, unsubstituted or $C_1$–$C_4$alkyl-substituted diphenylyl, naphthyl, phenanthenyl or pyridinyl, or a radical of formula

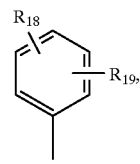

(VII)

Z and Z' are each independently of the other hydrogen halogen, $C_1$–$C_3$alkyl or $OR_7$, $R_1$, $R_5$ and $R_7$ are each independently of one another $C_1$–$C_4$alkyl, and $R_6$ is a radical of formula

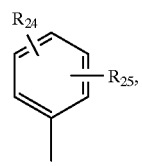

(VIII)

and $R_{15}$, $R_{16}$, $R_{18}$, $R_{19}$, $R_{24}$ and $R_{25}$ are each independently of one another a hydrogen, chloro or bromo atom, a methyl, cyano, nitro, alkylamino or alkoxy group containing 1–4 carbon atoms, a phenoxy group which is unsubstituted or substituted by chloro or methyl, a hydroxycarbonyl group, an alkoxycarbonyl or alkylcarbamoyl group containing 2–5 carbon atoms, or a phenylcarbamoyl group which is unsubstituted or substituted by chloro, methyl or methoxy.

4. A compound according to claim 3, wherein $R_{15}$, $R_{18}$ and $R_{24}$ are in p-position, and $R_{16}$, $R_{19}$ and $R_{25}$ are hydrogen.

5. A compound according to claim 4, wherein $R_{15}$, R18 and $R_{24}$ are each independently of one another methyl, chloro, cyano or methoxy.

6. A compound according to claim 1, of formula I, wherein R=R', X=X', Y=Y' and Z=Z'.

7. A compound according to claim 1, of formula

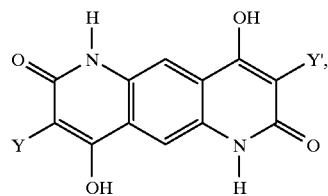

(IX)

wherein Y and Y' are equal and are diphenylyl, naphthyl, phenantrenyl, pyridinyl or a radical of formula

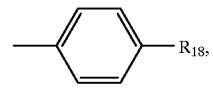

wherein $R_{18}$ is hydrogen, methoxy, chloro, bromo, cyano, nitro, dimethylamino, hydroxycarbonyl or methoxycarbonyl.

8. A composition, which comprises a high molecular weight organic material and a compound of formula (I) according to claim 1.

9. A method of colouring a high molecular weight organic material, which comprises incorporating a tinctorially effective amount of the compound of formula (I) according to claim 1.

* * * * *